United States Patent [19]

Appleton et al.

[11] Patent Number: 5,625,209
[45] Date of Patent: Apr. 29, 1997

[54] SILICON BASED SENSOR APPARATUS

[75] Inventors: Mark Appleton, Bedford, England; William R. Krenik, Garland, Tex.

[73] Assignee: Texas Instruments Incorporated, Dallas, Tex.

[21] Appl. No.: 434,816

[22] Filed: May 4, 1995

Related U.S. Application Data

[63] Continuation of Ser. No. 894,894, Aug. 26, 1992, abandoned.

[51] Int. Cl.$^6$ .................................................. H01L 23/58
[52] U.S. Cl. ..................... 257/253; 257/414; 257/469; 204/411; 204/421; 204/432; 340/634
[58] Field of Search ................................ 257/414, 253, 257/469; 204/411, 421, 432; 340/534

[56] References Cited

U.S. PATENT DOCUMENTS

| | | | |
|---|---|---|---|
| 4,180,771 | 12/1979 | Guckel | 257/253 X |
| 4,505,799 | 3/1985 | Baxter | 257/253 X |
| 4,592,824 | 6/1986 | Smith et al. | 257/414 X |
| 4,636,827 | 1/1987 | Rudolf | 257/253 |
| 5,457,333 | 10/1995 | Fukui | 257/253 |

FOREIGN PATENT DOCUMENTS 61-218932   9/1986   Japan ................................ 257/253

*Primary Examiner*—William Mintel
*Attorney, Agent, or Firm*—W. Daniel Swayze, Jr.; W. James Brady, III; Richard L. Donaldson

[57] ABSTRACT

A biomedical sensor (20) is formed on a semiconductor substrate (22). Insulated dielectric layers (23, 24) are formed on the face and backside of the semiconductor substrate (22). Metal leads (26, 28) contact the substrate (22) through openings in the dielectric layer (23). The leads (26, 28) are also each connected to a set of interleaved longitudinal contact fingers (27, 29). A pair of contacts (30, 32) are formed on the opposite side of the substrate (22) from the contact figures (27, 29). A conductive biologic sample is placed over the interleaf fingers (27, 29), electrical measurements can be made through backside contacts (30, 32) so resistance measurements can be taken.

11 Claims, 6 Drawing Sheets

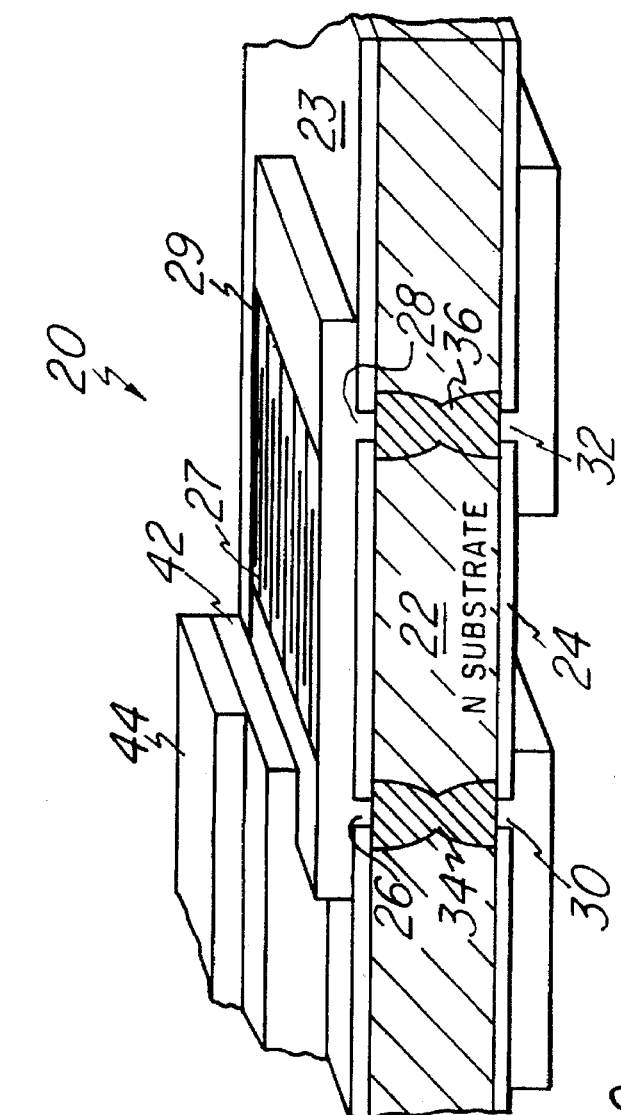
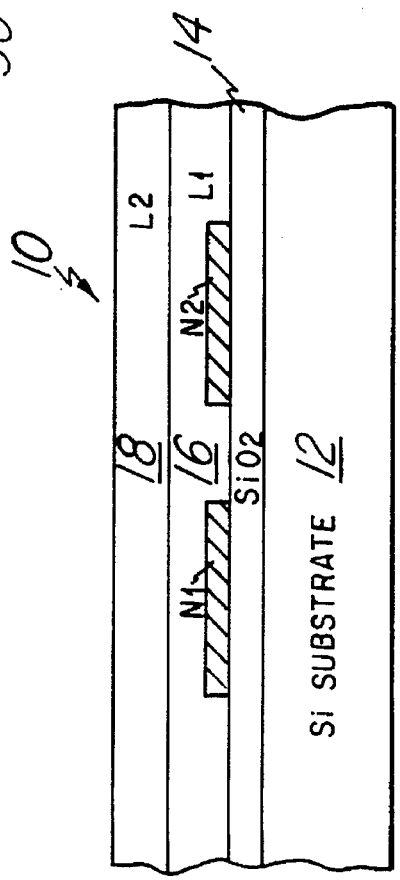
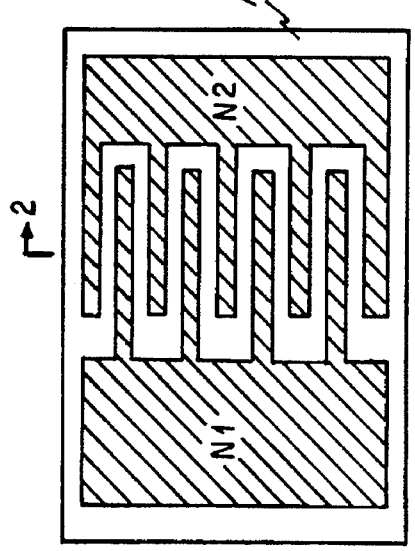
Fig.1 (PRIOR ART)
Fig.2 (PRIOR ART)
Fig.3

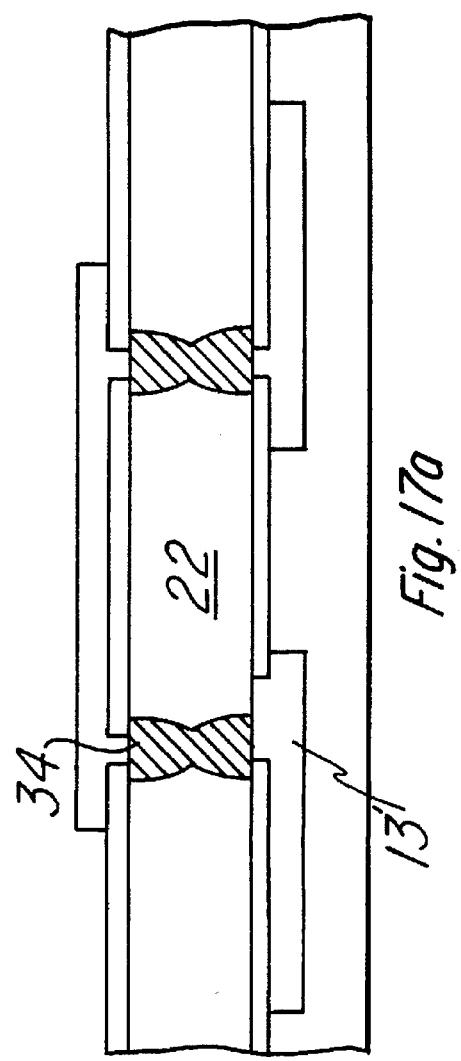
Fig. 17a
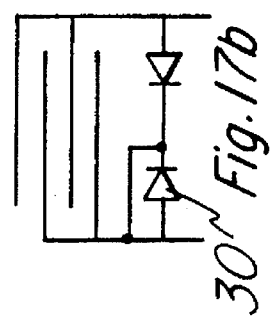
Fig. 17b
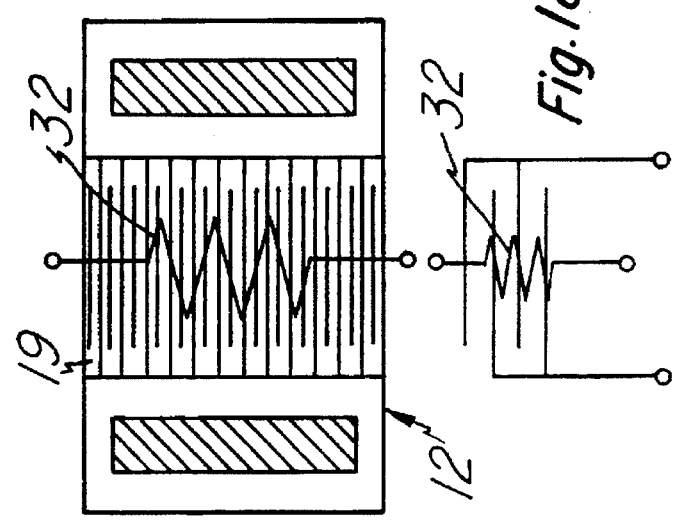
Fig. 18a
Fig. 18b

SILICON BASED SENSOR APPARATUS

This is a continuation of application Ser. No. 07/894,894, filed Aug. 26, 1992, now abandoned.

FIELD OF THE INVENTION

This invention relates to the field of diagnostic medical sensors.

BACKGROUND OF THE INVENTION

The use of sensor technology in the diagnostic medical area is a rapidly expanding field. The use of such sensors can provide a quick and inexpensive method of testing for such things as blood glucose levels by means of resistance measurements.

A prior art sensor is shown in FIGS. 1 and 2. Leads N1 and N2 are formed on the surface of the sensor. An enzyme polymer layer L1 and overcoat L2 (FIG. 2) are formed over the leads. A droplet of blood is applied to the surface of the sensor, causing a reaction with the enzyme layer L1 and the resistance between the leads is measured. This offers a faster, easier and more accurate blood glucose reading than current photo-optic methods. One major problem with silicon based sensors is the cost. Since each sensor will only be used once and then discarded, the cost must be very low.

The major problem which must be overcome in building such a sensor is that the polymer material is very delicate and cannot be subjected to heat or chemicals needed to pattern it. Thus, a method of connecting to terminals N1 and N2 without disturbing the polymer is required. One such prior art method involved etching through the slice and providing backside contacts. This technique, however, leads to high manufacturing costs due to stress and breakage of slices.

BRIEF DESCRIPTION OF THE DRAWINGS

FIG. 1 is a top view of a prior art biomedical sensor;

FIG. 2 is a cross-sectional figure taken along line 2—2 of FIG. 1; and

FIG. 3 is a cross-sectional view of a biomedical sensor made in accordance with the present invention.

FIGS. 16, 17a, 17b, 18a, 18b show alternative embodiments of the present invention.

DETAILED DESCRIPTION OF THE PREFERRED EMBODIMENT

Figure 4:
FIGS. 4–15 show the sensor of FIG. 3 at various stages of the process flow.

Referring now to FIGS. 1 & 2, there is shown a prior art biosensor device 10. The biosensor 10 is typically formed on a silicon substrate 12, and has a pair of leads N1 and N2, which are preferably metal. The leads N1 and N2 are formed on an insulating layer 14 formed on the surface of substrate 12. A polymer enzyme layer 16 is formed over the leads N1 and N2. A polymer overcoat 18 is then formed over the polymer enzyme layer 16.

To use the sensor, a blood sample is placed on the polymer overcoat and the resistance between leads N1 and N2 is measured. The resistance measurement provides a measure of the blood glucose levels as a result of the interaction between the blood sample and the polymer enzyme.

In order to measure the resistance between the leads N1 and N2, it is necessary to make backside contact with the leads, so as to not disturb the outer surface of the sensor 10.

Referring now to FIG. 3, there is shown a cross-section of a sensor 20 made in accordance with the present invention. The sensor is formed on a semiconductor substrate 22, which is N-type silicon in the preferred embodiment. Dielectric layers 23 and 24 are formed on the face sad backside of substrate 22, respectively. Metal leads 26 and 28 contact the substrate 22 through openings in dielectric layer 23. The leads 26 and 28 are, also each connected to a set of interleaved longitudinal contact fingers 27 and 29. While the sets of fingers 27 and 29 are interleaved, they are not in electrical contact with each other.

A pair of backside contacts 30 and 32 are formed on the dielectric layer 24, and contact the substrate 22 through contact holes in dielectric layer 24. In the preferred embodiment, dielectric layers 23 and 24 are oxide but could also be other dielectric material.

Backside contact 30 is in ohmic contact with metal lead 26 through a conductive region 34. Conductive region 34 extends through substrate 22 and is preferably formed by diffusing a P-type dopant through substrate 22.

Backside contact 32 is likewise in ohmic contact with lead 28 through conductive region 36, which is preferably formed when region 34 is formed.

FIGS. 4–15 show the process flow of the present invention in detail. It is to be understood that the detailed drawings of the process flow are illustrative only, and are not to scale. Referring to FIG. 4, the process starts with a silicon substrate 22. In the preferred embodiment the :substrate 22 is 10 to 11 mils thick, with both the front side and the backside etch polished. The preferred embodiment is formed on a 3" wafer, although other size wafers could be used. The substrate could also alternatively be greater than 11 mils, with the thickness reduced to the desired 10–11 mils by front and/or backside polishing.

Figure 5:
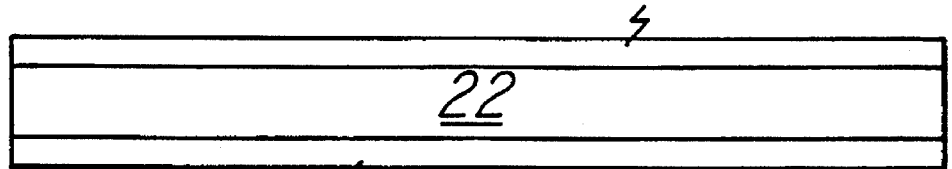

FIG. 5 shows the substrate 22 after an oxidation step has been performed, forming barrier oxide layers 23 and 24 on the front and backside of substrate 22. The oxide layers 23 and 24 preferably have a minimum thickness of approximately 8000 Å. The substrate is placed in a dry Oxygen ambient at approximately 1100° C. for 10 minutes, followed by 230 minutes in a wet O2 ambient, followed by 5 minutes dry O2.

Figure 6:
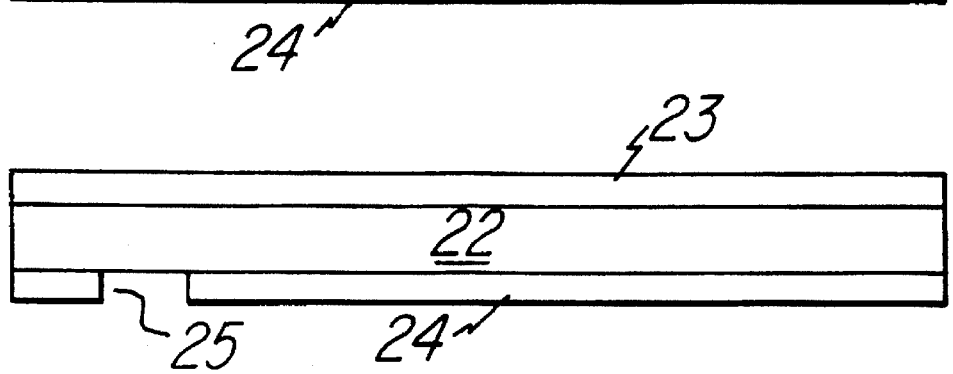
Figure 7:
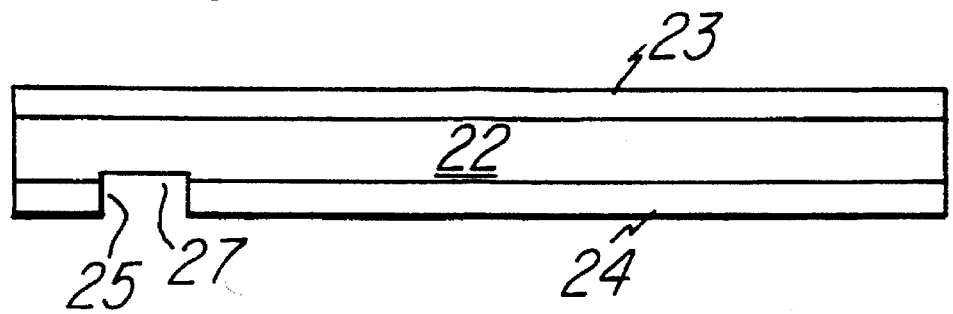

An opening 25 is then etched through oxide layer 24 on the backside of substrate 22, as shown in FIGS. 6 & 7. After the opening 25 is formed the silicon substrate 22 is etched to a depth of 2.0 to 15.0 µm, and preferably to a depth of 10 µm, as shown in FIG. 7. The registration mark 27 etched in silicon substrate 22 is used to align the masks used to mask the backside of the substrate 22 to ensure that the through diffusion described below, as well as the backside contacts are properly aligned with the contacts formed on the frontside of the substrate 22.

The oxide removal and registration etch steps described above could alternatively be omitted if there were some mechanical fixture established to ensure alignment between later oxide removal steps, or if some type of marking were placed on the substrates prior to processing to ensure alignment.

Figure 8:
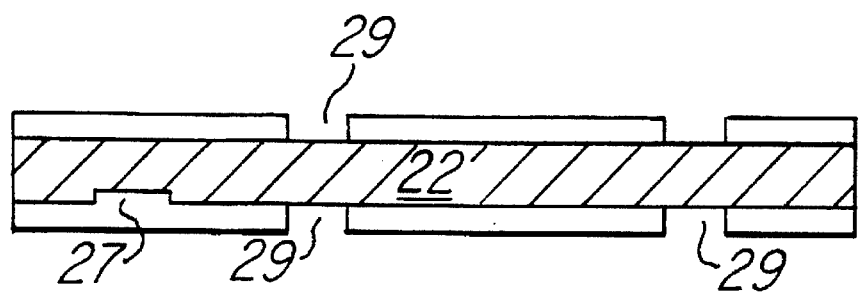
Figure 9:
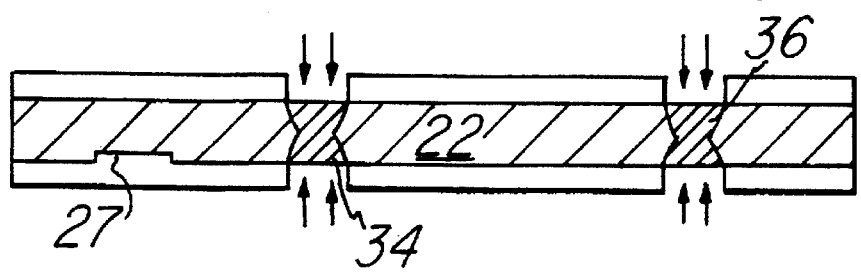

As shown in FIG. 8, windows 29 are then formed through the oxide layers 23 and 24 on the face and backside of substrate 22. Impurities are then deposited or implanted through windows 29, as shown in FIG. 9, and the impurities are diffused to form diffused regions 34 and 36 extending from the face to the back side of substrate 22. In the preferred embodiment, the diffusion is p-type, with Boron being deposited in contact windows 29, and then diffused at a temperature of 1300° C. for 157 hours. As can be seen, the diffusion step creates conductive regions of p-type material 34 and 36 extending from the face to the backside of substrate 22.

As an alternative, portions of the backside of the substrate 22 could be etched away in the area of windows 29 to decrease the thickness of the substrate 22 in the regions where the conductive diffusions will be made. This would reduce the diffusion time required to merge the front and back diffusions and could also be used to reduce the impedance between front and back.

Figure 10:
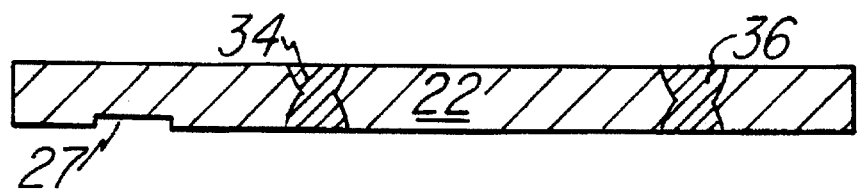
Figure 11:
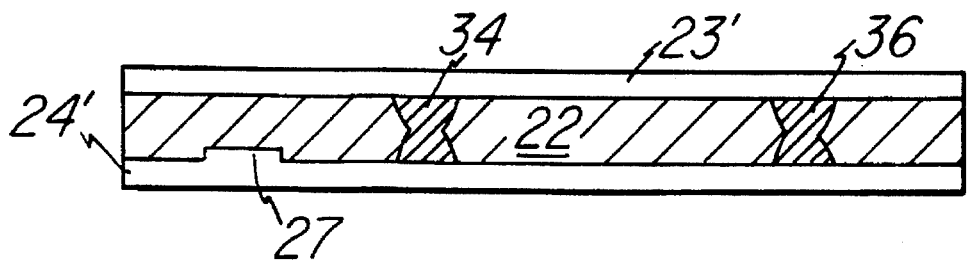

After the diffusion is complete, the oxide grown during the diffusion is stripped, preferably with a wet HF solution, leaving the substrate 22 as shown in FIG. 10. A layer of oxide 23 and 24 is then grown on the face and back of the substrate 22 as shown in FIG. 11, with a thickness of approximately 1000 Å.

Figure 12:
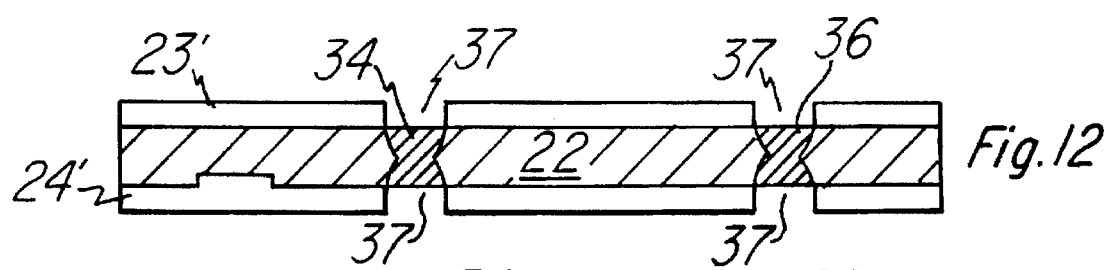
Figure 13:
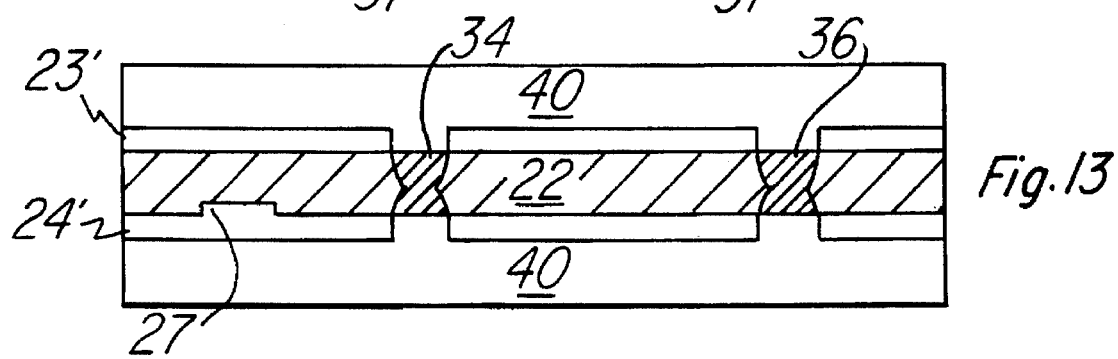
Figure 14:
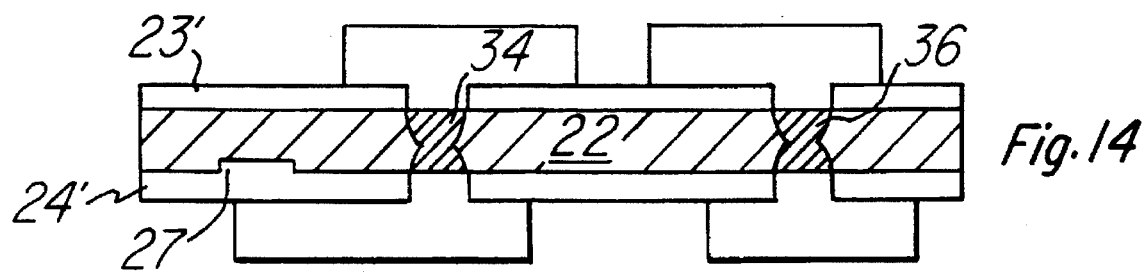

Contact windows 37 are then formed through oxide layers 23 and 24 as shown in FIG. 12, and a conductive (preferably metal) layer 40 is then formed over the front and back sides of the substrate 22. In the preferred embodiment, 500 Å of Chromium is deposited, followed by 500 Å of Gold. Other conductive materials, such as Titanium, could be substituted for the Chromium.

In some cases it might be necessary to perform additional process steps to achieve the desired ohmic contact between the metal layers 40 and the p-type diffusions 34 and 36. In order to achieve greater ohmic contact, an additional process step adding a p-type deposition prior to metallization can be added. The p-type deposition is performed during the process as shown in FIG. 12, after contact openings 37 are made. The process steps shown in FIGS. 10, 11 and 12 are then repeated.

Figure 15:
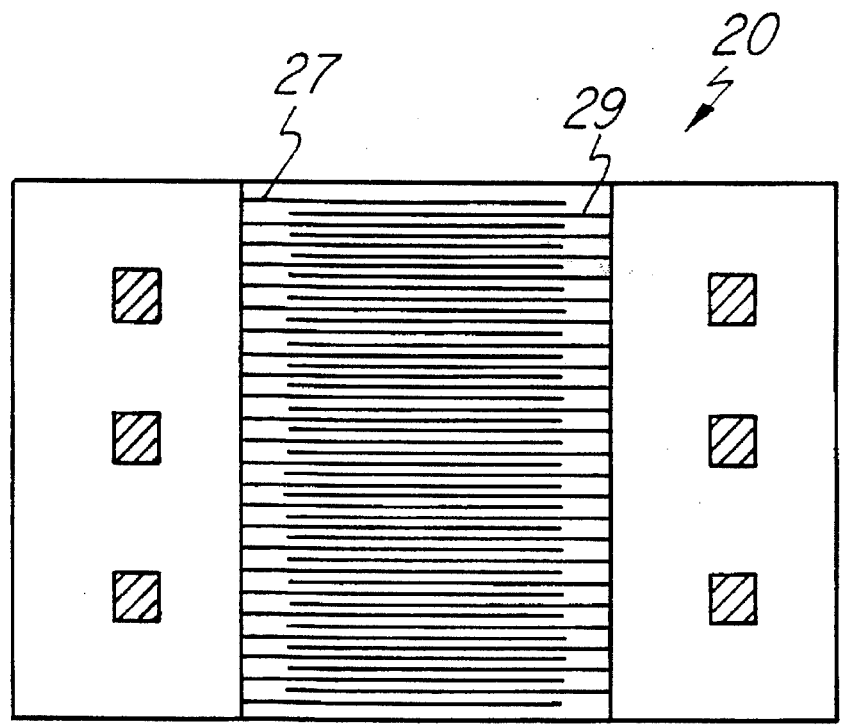

Once the metal layers 40 are deposited, the metal is patterned, forming backside contacts 30 and 32. On the frontside of the substrate, interleaved sets of metal fingers 27, 29 are formed, as shown in FIG. 15.

The metal fingers 27, 29 can be formed, by example, by putting down a layer of chromium, then a layer of gold, patterning, rand performing a stack etch. Other methods could also be used, such as patternig the chromium layer and coating it with gold. Other metals could be used in place of the chromium, such as aluminum.

In the preferred embodiment, referring again to FIG. 3, the metal leads on the substrate 22 are then covered with a polymer ,enzyme layer 42, which is in turn covered with a polymer overcoat 44. The polymer enzyme layer 42 is reactive with human blood, enabling a measurement of the blood sugar level based upon the resistance between leads 27, 29.

The enzyme overcoat 44 and the enzyme layer 42 also act as sort of a sponge to hold the blood sample in the area of the sensor so that readings can be token without the blood sample running off the sensor.

In use, a small sample of blood is spread over the face of the sensor 20. The sensor 20 is then placed in a device (not shown) having contacts in electrical communication with backside contacts 30 and 32 so resistance measurements can be taken, from which a blood sugar measurement can be extrapolated.

Figure 16:
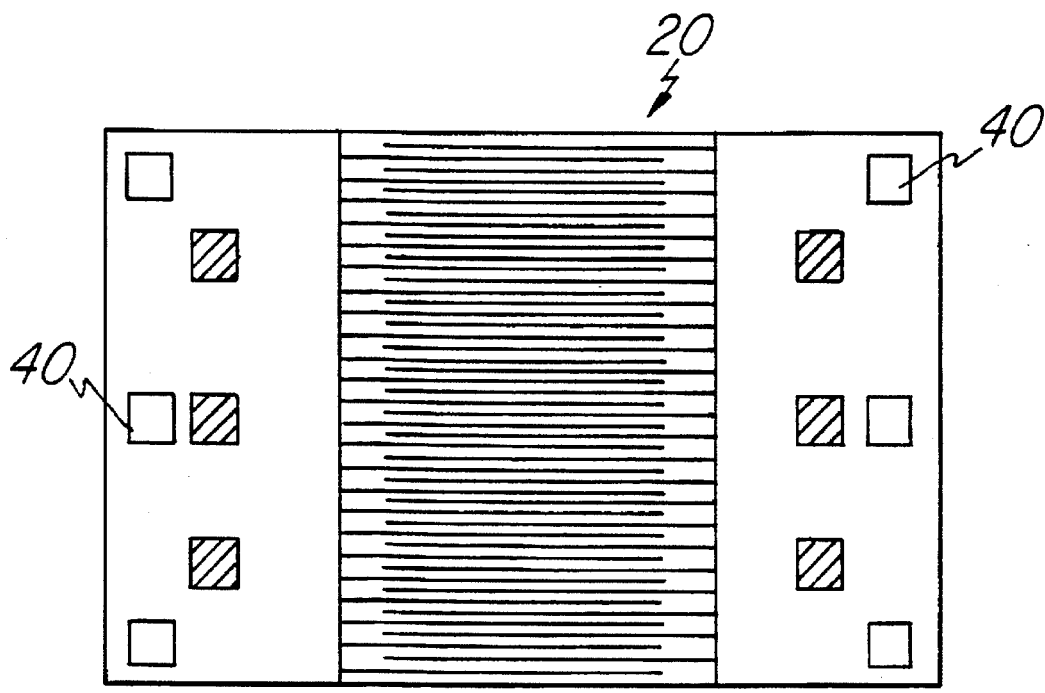

An alternative embodiment of the present invention is shown in FIG. 16. In order to ensure that the sensor functions properly, it is important to thoroughly wet the surface of the sensor. In the alternative embodiment, auxiliary sensors 40 are formed around the periphery of the sensor 20. The auxiliary sensors 40 are smaller than the main sensor 20, but are preferably formed using the same process steps as sensors 20.

Since reading the sensor is a simple DC resistance measurement, the auxiliary sensors 40 would be read in turn and the values compared. If the measurements from the auxiliary sensors 40 were not within a prespecified range, which would indicate that the entire surface of the sensor 20 had not been wetted with blood, an error condition would be indicated to the user. Yet another alternative embodiment (not shown) would be to form a distributed peripheral sensor.

It is also desirable that the biosensor be equipped so that the resistance measurements made can be calibrated against the temperature of the biosensor. An embodiment which would allow temperature compensation is shown in FIG. 17a. FIG. 17a shows the sensor of FIG. 3, with one of the p-diffusion areas 23 shorted to the substrate to form a diode 30. In the alternative embodiment, the substrate connection is made by etching a larger contact hole 13', as shown in FIG. 17a.

The voltage shift is then calibrated against temperature (approximately 2 mV/°C.). This arrangement is shown schematically in FIG. 17b.

A second method of calibrating the sensor 10 against temperature shifts is shown in FIG. 18a and 18b. In this method, a diffused resistor 32 is formed in the substrate 12 under the interlocking metal fingers 19, which form the portions of the contacts between which the resistance is measured. The diffused resistor 32 is formed by well known diffusion techniques. The diffused resistor is shown schematically in FIG. 18b.

Yet a third method is to form a bridge network of diffused resistors under the interleaved fingers to give resistor ratio changes during temperature shifts. This embodiment would require a reference resistor on the substrate, and would also require four terminals.

In the preferred embodiment of the invention, the sensors are separated, and packaged so that individual sensors are available for use when needed. However, in an alternative embodiment, a plurality of sensors is packaged together as an individual unit, with circuitry on the substrate itself for selecting the individual sensor and performing the electrical measurements.

When the circuitry connecting the individual sensors to the sensing/measuring circuitry is formed, it can either be formed on the face of the substrate with through diffusions for backside connections to the external circuitry, or on the backside of the wafer, with through diffusions for connecting the sensors to the circuitry.

in such a system, a multiplexor for electronically selecting an individual sensor is provided, as well as a microprocessor or similar circuit for performing the measurements. The system also includes a gasket/cover arranged so that individual sensors can be accessed for exposure to a blood sample. The multiplexor circuitry connects the selected sensor to the processor. In this manner a disposable unit is provided, with sufficient sensors to last a convenient length of time.

We claim:

1. A biosensor, comprising:

a semiconductor substrate having a first side and a second side;

a first contact region on the first side of the substrate to directly connect to the biosensor;

a second contact region on the second side of the substrate; and conductive region extending from the contact region on the first side to the second contact region on the second side.

2. A biosensor on a semiconductor substrate, comprising:

a first and second contact region formed on a first side of the substrate to directly connect to the biosensor;

a first and second contact region formed on a second side of the substrate; and a pair of conductive regions extending through the substrate, each providing an ohmic connection between the one of the contact regions on the first side and one of the contact regions on the second side.

3. The biosensor of claim 2, further comprising:

a pair of metal leads, one connected to the first contact region, the other connected to the second contact region.

4. The biosensor of claim 2, further comprising:

a plurality of longitudinal metal leads on the first side of the substrate, a first set attached to the first contact region, and a second set attached to the second contact region, the first set being interspersed with the second set.

5. The biosensor of claim 4, further comprising:

a coating formed over the metal leads, the coating being reactive with a biological substance placed thereon.

6. The biosensor of claim 5, wherein the biosensor is a blood sensor.

7. A biosensing system formed on a semiconductor substrate, comprising:

a plurality of pairs of contacts on a first side of the substrate to directly to the biosensing system;

a plurality of pairs of contacts on a second side of the substrate, each of said pairs associated with a pair of contacts on the first side;

a plurality of pairs of conductive regions through the substrate, each of said conductive regions making ohmic contact between one of a pair of contacts on the first side and one of the pair of contacts on the second side of the substrate; an analysis circuit on the backside of the substrate for performing electrical measurements between the contacts on the second side of the wafer; and a circuit for selectively connecting one of the pairs of contacts on the second side of the substrate to the analysis circuit.

8. The biosensor of claim 7, further comprising:

a coating over the first side of the substrate, the coating being reactive with a biologic agent being applied to the coating.

9. The biosensor system of claim 7, further comprising:

a plurality of sets of interleaved longitudinal metal leads formed on the first side, each set being associated with a pair of contacts on the face, each one of said associated sets being connected to one of the pairs of contacts.

10. The biosensor system of claim 7, further comprising:

means for applying a biologic agent to a single one of said sensor regions.

11. The biosensor system of claim 7, further comprising:

circuitry for temperature compensation formed on the substrate.

* * * * *